(12) United States Patent
Carpentier et al.

(10) Patent No.: US 8,519,070 B2
(45) Date of Patent: Aug. 27, 2013

(54) POST-METALLOCENE COMPLEXES BASED ON BIS(NAPHTHOXY)PYRIDINE AND BIS(NAPHTHOXY)THIOPHENE LIGANDS FOR THE POLYMERISATION OF ETHYLENE AND ALPHA-OLEFINS

(75) Inventors: Jean-François Carpentier, Acigne (FR); Evgueni Kirillov, Rennes (FR); Abbas Razavi, Mons (BE)

(73) Assignees: Total Petrochemicals Research Feluy, Seneffe (Feluy) (BE); Centre National de la Recherche Scientifique (CNRS), Paris (FR)

( * ) Notice: Subject to any disclaimer, the term of this patent is extended or adjusted under 35 U.S.C. 154(b) by 311 days.

(21) Appl. No.: 12/919,248

(22) PCT Filed: Feb. 17, 2009

(86) PCT No.: PCT/EP2009/051868
§ 371 (c)(1), (2), (4) Date: Jan. 11, 2011

(87) PCT Pub. No.: WO2009/106458
PCT Pub. Date: Sep. 3, 2009

(65) Prior Publication Data
US 2011/0144291 A1    Jun. 16, 2011

(30) Foreign Application Priority Data
Feb. 25, 2008  (EP) .................................... 08290185

(51) Int. Cl.
*C08F 4/76* (2006.01)
*C08F 4/64* (2006.01)
*B01J 31/38* (2006.01)
*C07F 7/00* (2006.01)

(52) U.S. Cl.
USPC ........... 526/172; 526/161; 526/160; 526/170; 526/348; 526/352; 556/51; 502/113

(58) Field of Classification Search
USPC .................................... 556/51; 526/172, 161
See application file for complete search history.

(56) References Cited

U.S. PATENT DOCUMENTS

2003/0191015 A1* 10/2003 Chi-Wang Chan et al. .. 502/150
2011/0112273 A1*  5/2011 Carpentier et al. ........... 528/272

FOREIGN PATENT DOCUMENTS

| EP | 0 606 125 A2 | 7/1994 |
| JP | 06-192330 A | 7/1994 |
| JP | 2004-291253 A | * 10/2004 |
| WO | 2008/036882 A1 | 3/2008 |

OTHER PUBLICATIONS

Sweetman et al., Tetrahedron Letts. 2005, 46, 4663-4646.*
Chan et al., J. Chem. Soc., Dalton Trans., 2002, 3085-3087.*
Kirillov, E.; Roisnel, T.; Razavi, A.; Carpentier, J.-F. Organometallics, 2009, 28, 5036-5051.*
Chan, Michael C. W. et al., "Surprising Activity for Group 4 Polyolefin Catalysts [M{(OAr)2py}Cl2(thf)] (M= Zr, Ti) Bearing Tridentate Pyridine-2,6-bis(aryloxide) Ligands" Journal of The Chemical Society. Dalton Transactions, Aug. 21, 2002, No. 16, pp. 3085-3087, XP002486339.

(Continued)

*Primary Examiner* — Rip A. Lee

(57) ABSTRACT

The present invention relates to the field of group 4 post-metallocene complexes based on sterically encumbered bis(naphthoxy)pyridine and bis(naphthoxy)thiophene ligands. It also relates to the use of such post-metallocene complexes in the polymerization of ethylene and alpha-olefins.

11 Claims, 9 Drawing Sheets

(56) References Cited

OTHER PUBLICATIONS

Chan, Michael C. W. et al., "Synthesis, Structures, and Olefin Polymerization Characteristics of Group 4 Catalysts [Zr{(OAr)2py}Cl2(D)] (D= O-Donors, Cl[HPR3]) Supported by Tridentate Pyridine-2,6-bis(aryloxide) Ligands" Organometallics, Jan. 30, 2006, vol. 25, No. 3, pp. 785-792, XP002486340.

Sweetman, B. A. et al., "Synthesis, Resolution and Racemisation Studies of New Tridentate Ligands for Asymmetric Catalysis" Tetrahedron Letters, Elsevier, Amsterdam, Jul. 4, 2005, vol. 46, No. 27, pp. 4643-4646, XP004925566.

International Search Report issued in PCT/EP2009/051868 mailed on May 8, 2009 (3 pages).

Patent Abstracts of Japan, Japanese Publication No. 06192330, Publication Date: Jul. 12, 1994 (1 page).

* cited by examiner

A

B

C

D

E

F

Z = heteroatom
n = 0, 1
R = bulky group

US 8,519,070 B2

POST-METALLOCENE COMPLEXES BASED ON BIS(NAPHTHOXY)PYRIDINE AND BIS(NAPHTHOXY)THIOPHENE LIGANDS FOR THE POLYMERISATION OF ETHYLENE AND ALPHA-OLEFINS

CROSS-REFERENCE TO RELATED APPLICATIONS

This application claims the benefit of PCT/EP2009/051868, filed Feb. 17, 2009, which claims priority from EP 08290185.1, filed Feb. 25, 2008.

The present invention relates to the field of post-metallocene complexes based on sterically encumbered bis(naphthoxy)pyridine and bis(naphthoxy)thiophene ligands. It also relates to the use of such post-metallocene complexes in the polymerisation of ethylene and alpha-olefins.

There is a need for new highly active alkene polymerisation catalyst systems based on post-metallocenes and a lot of research has been carried out in that field, such as reviewed for example in Gibson and Sptizmesser (Gibson, V. C.; Spitzmesser, S. K. in Chem. Rev. 2003, 103, 283) or in Ittel et al. (Ittel, S. D.; Johnson, L. K.; Brookhart, M. in Chem. Rev. 2000, 100, 1169 or in Britovsek et al. (Britovsek, G. J. P.; Gibson, V. C.; Wass, D. F. in Angew. Chem., Int. Ed. 1999, 38, 429).

Among the plethora of newly disclosed catalytic systems, discrete group 4 metal complexes bearing various chelating aryloxide-based ligands have demonstrated astonishing performances in the polymerisation of ethylene and α-olefins. In particular, industry-relevant highly effective phenoxy-imine systems were pioneered by Fujita et al. at Mitsui, such as disclosed for example in Makio and Fujita (Makio, H.; Fujita. T. in Macromol. Rapid Commun. 2007, 28, 698) or in Terao et al. (Terao, H.; Ishii, S.; Saito, J.; Matsuura, S.; Mitani, M.; Nagai, N.; Tanaka, H.; Fujita, T. in Macromolecules 2006, 39, 8584) or in Nakayama et al. (Nakayama, Y.; Saito, J.; Bando, H.; Fujita, T. in Chem. Eur. J. 2006, 12, 7546) or in Saito et al. (Saito, J.; Suzuki, Y.; Makin, H.; Tanaka. H.; Onda, M.; Fujita, T. in Macromolecules 2006, 39, 4023) or in Nakayama et al. (Nakayama, Y.; Saito, J.; Bando, H.; Fujita, T. in Macromol. Chem. Phys. 2005, 206, 1847) or in Furuyama et al. (Furuyama, R.; Saito, J.; Ishii, S.; Makio, H.; Mitani, M.; Tanaka, H.; Fujita, T. in J. Organomet. Chem. 2005, 690, 4398) or in Saito et al. (Saito, J.; Tohi, Y.; Matsukawa, N.; Mitani, M.; Fujita, T. in Macromolecules 2005, 38, 4955). Typical metallic complexes of this family are represented in, FIG. 1, complex A Other groups also reported very active highly isospecific 1-hexene polymerization precursors bearing tetradentate {ONXO} and {ONNO} auxiliaries such as described for example in Mason and Coates (Mason, A. F.; Coates, G. W. in J. Am. Chem. Soc. 2004, 126, 10798) or in DeRosa et al. (DeRosa, C.; Circelli, T.; Auriemma, F.; Mathers, R. T.; Coates, G. W. in Macromolecules 2004, 37, 9034) or in Mason and Coates (Mason, A. F.; Coates, G. W. in J. Am. Chem. Soc. 2004, 126, 16326) or in Reinartz et al. (Reinartz, S.; Mason, A. F.; Lobkovsky, E. B.; Coates, G. W. in Organometallics 2003, 22, 2542) or in Hustad et al. (Hustad, P. D.; Tian, J.; Coates, G. W. in J. Am. Chem. Soc. 2002, 124, 3614) or in Yeori et al. (Yeori, A.; Goldberg, I.; Shuster, M.; Kol, M. in J. Am. Chem. Soc. 2006, 128, 13062). Further structures have been described in Groysman et al. (Groysman, S.; Sergeeva, E.; Goldberg, I.; Kol, M. in Inorg. Chem. 2005, 44, 8188) or in Yeori et al. (Yeori, A.; Groysman, S.; Goldberg, I.; Kol, M. in Inorg. Chem. 2005, 44, 4466) or in Segal et al. (Segal, S; Goldberg, I; Kol, M. in Organometallics 2005, 24, 200) or in (Yeori, A; Gendler, S; Groysman, S.; Goldberg, I.; Kol, M. in Inorg. Chem. Commun. 2004, 7, 280) or in Tshuva et al. (Tshuva, E. Y.; Groysman, S.; Goldberg, I.; Kol, M.; Goldschmidt, Z. in Organometallics 2002, 21, 662). Typical structures of this family are represented in FIG. 1, complexes B and C. Stereorigid complexes incorporating tetradentate {OSSO} ligands were shown to effectively produce isotactic polystyrene such as described for example in Lian et al. (Lian, B.; Beckerle, K.; Spaniol, T. P.; Okuda, J. in Angew. Chem., Int. Ed. 2007, 46, 8507) or in beckerle et al. (Beckerle, K.; Manivannan, R.; Lian. B.; Meppelder, G.- J. M.; Raabe, G.; Spaniol, T. P.; Ebeling, H.; Pelascini, F.; Muelhaupt, R.; Okuda, J. in Angew. Chem., Int. Ed. 2007, 46, 4790) or in Beckerle et al. (Beckerle, K.; Manivannan, R.; Spaniol, T. P.; Okuda, J. in Organometallics 2006, 25, 3019) or in Capacchione et al. (Capacchione, C.; Manivannan, R.; Barone, M.; Beckerle, K.; Centore, R.; Oliva, L.; Proto, A.; Tuzi, A.; Spaniol, T. P.; Okuda, J. in Organometallics 2005, 24, 2971). Typical structures of this group are represented in FIG. 1, complex D. Recently, rigid tridentate ligand systems and related polymerisation systems were introduced: they enable the formation of HDPE with activities of the order of 10-15 $10^6$ kg·mol$^{-1}$·h$^{-1}$ as well as ethylene/1-octene copolymerization. they are described for example in Chan et al. (Chan, M. C. W.; Kui, S. C. F.; Cole, J. M.; McIntyre, G. J.; Matsui, S.; Zhu, N.; Tam, K.- H. in Chem. Eur. J. 2006, 12, 2607) or in Chan et al. (Chan, M. C. W.; Tam, K.- H.; Zhu, Z.; Chiu, P.; Matsui, S. in Organometallics, 2006, 25, 785) or in Chan et al. (Chan, M. C. W.; Tam, K.- H.; Pui, Y.- L.; Zhu, Z. in J. Chem. Soc., Dalton Trans. 2002, 3085). Typical structures of this group are represented in FIG. 1, complexes E and F.

LIST OF FIGURES

Figure 1:
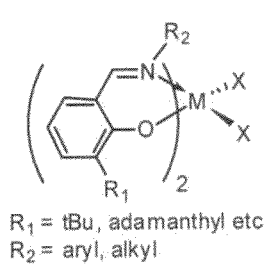
FIG. 1 represents various organometallic compounds disclosed in literature that are suitable for the oligomerisation or polymerisation of ethylene and alpha-olefins.
Figure 1:
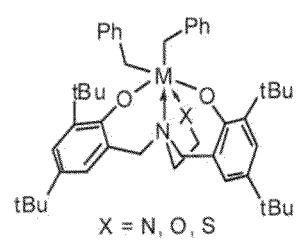
Figure 1:
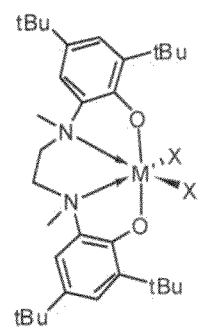
Figure 1:
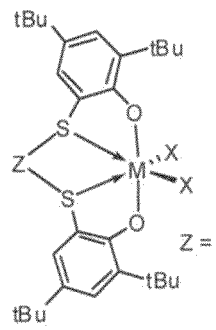
Figure 1:
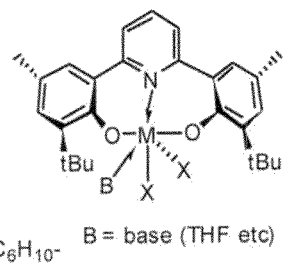
Figure 1:
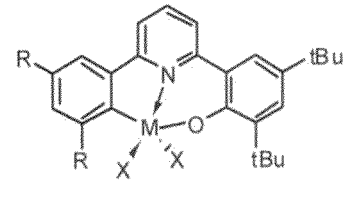

There is however still a need to develop new very active catalyst systems having specific functionalities in order to tailor polymer with desired properties.

It is an aim of the present invention to prepare sterically encumbered ligands based on phenoxy groups.

It is another aim of the present invention to complex these ligands with metals with firm stereoselective coordination.

it is also an aim of the present invention to prepare very active catalyst systems for the polymerisation of ethylene and alpha-olefins.

Any one of these aims is, at least partially, fulfilled by the present invention.

Accordingly, the present invention discloses a pro-ligand of formula I

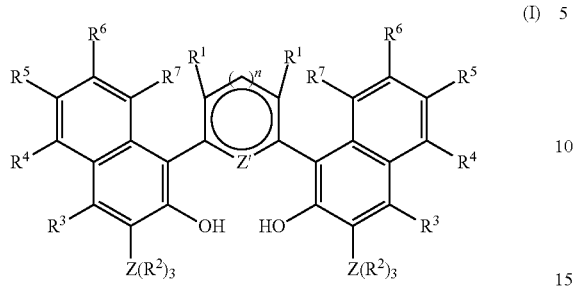

Wherein $R^1$, $R^3$, $R^4$, $R^5$, $R^6$ and $R^7$ are each independently selected from hydrogen, unsubstituted or substituted hydrocarbyl, or inert functional group, wherein two or more of said groups can be linked together to form one or more rings, wherein Z' is one or two heteroatom(s) and n is 0 (Z'=O, S, N=N) or 1 (Z'=N), wherein Z is an atom selected from group 14 of the Periodic Table, wherein $R^2$ is a substituted or unsubstituted aryl group having at most 8 carbon atoms, and/or an alkyl group, with the restriction that $Z(R^2)_3$ is a bulky group, at least as bulky as tertio-butyl.

$Z(R^2)_3$ can also be a substituted aryl group.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

Preferably $R^1$, $R^3$, $R^4$, $R^5$, $R^6$ and $R^7$ are each independently selected from hydrogen or alkyl groups having at most 6 carbon atoms, more preferably they all are hydrogen.

Preferably Z' is S or N or N=N.

Preferably, Z is C or Si, more preferably, it is Si.

Preferably $R^2$ is a substituted or unsubstituted phenyl group, or a higher aromatic group (e.g. naphthyl), or an alkyl. More preferably, it is an unsubstituted phenyl group or a tertio-butyl group.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

Several procedures have been tested in order to prepare the ligands of the present invention, most of them without success. They can be prepared in good yield starting from β-naphthol by a process that comprises the steps of:

a) providing β-naphthol of formula

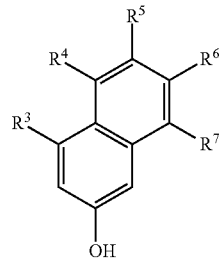

b) introducing alkoxy alkyl protecting groups by reacting with an alkoxy alkyl halide of formula XROR' wherein X is an halogen and R and R' are each independently selected from alkyl having from 1 to 6 carbon atom in the presence of dimethylformamide (DMF) and an alkali metal-alkyl or alkali metal-hydride, preferably NaH, to obtain a compound of formula;

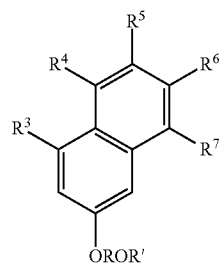

c) reacting with $(R^2)_3ZX'$, wherein X' is an halogen, in the presence of sec-BuLi in a solvent to obtain a compound of formula

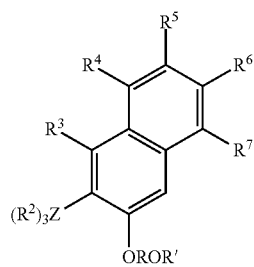

d) reacting with a dihaloheteroaryl of formula

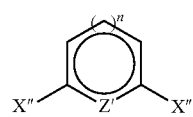

wherein Z' is one or two heteroatom(s) and n is 0 (Z'=O, S, N=N) or 1 (Z'=N), X" is an halogen (Cl, Br, I; preferably X"=Br), in the presence of a palladium or nickel cross-coupling catalyst in order to obtain a compound of formula

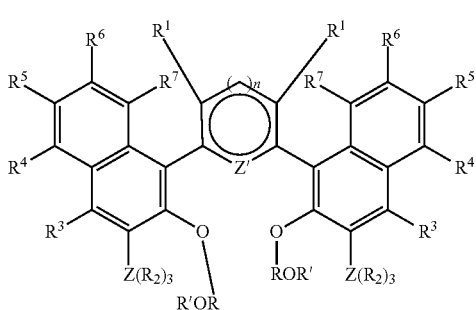

e) deprotecting the compound obtained in step d), e.g. by reaction of an acid (e.g. HCl in CHCl₃/EtOH), in order to obtain a bridged pro-ligand of general formula I

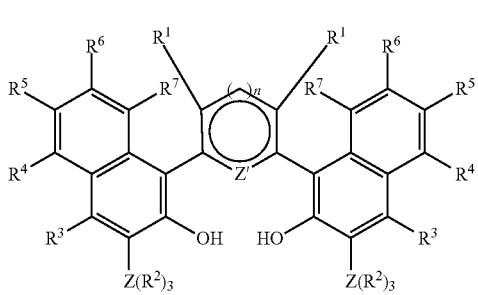

Figure 2:
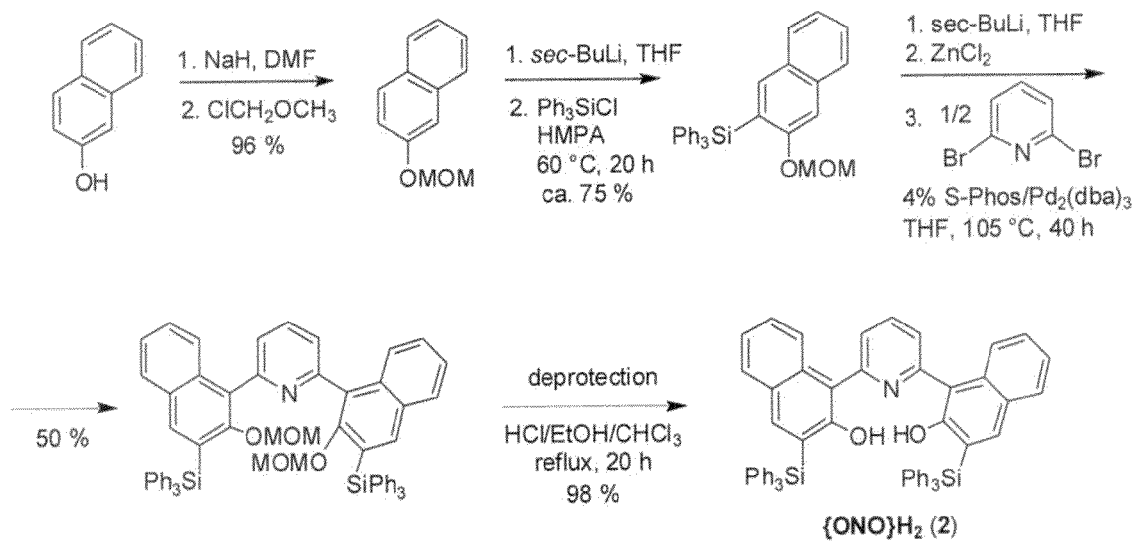
FIG. 2 represents the scheme used for the preparation of {ONO}N$_2$.

The method of preparation can be summarised in the scheme presented in exemplary FIG. 2, for the specific preparation of a given {ONO}H₂ pro-ligand.

Figure 3:
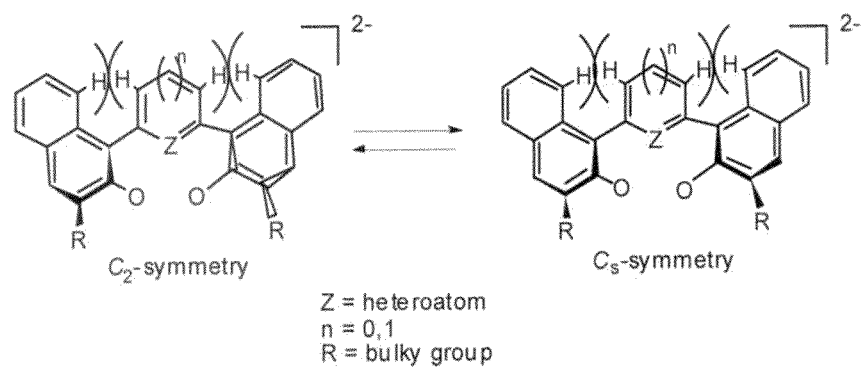
FIG. 3 represents the non coplanar orientation of the bridging heterocyclic and adjacent naphthyl groups resulting from the steric repulsion between protons at meta and 8 positions.

The key feature of the ligands according to the present invention is the possibility to form firm stereoselective coordination to the metal center provided by the non-coplanar orientation of the bridging heterocyclic and adjacent naphthyl groups due to steric repulsion between protons at meta and 8 positions of these moieties as can be seen in exemplary FIG. 3.

The invention also discloses a metallic complex of formula II

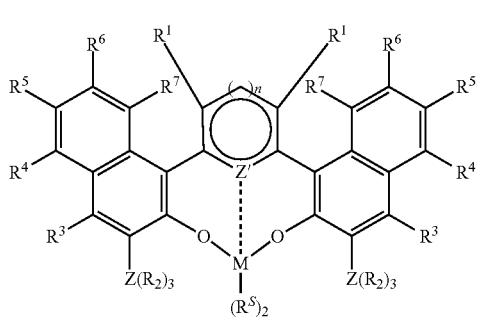

The metallic complexes II result from the complexation of pro-ligand I with metallic salts MR$ₙ in a solvent, wherein M is a metal Group 4 of the periodic Table, wherein each R$ is the same or different and is an alkyl, benzyl, aryl, amido, alkoxide, and/or halide (Cl, Br, I).

Preferably all R$ are the same and are either CH₂Ph, OiPr or NMe₂.

Preferably one equivalent of metallic salt is used per bridged bisnaphthol complex.

The metallation reaction is carried out at a temperature of from −80° C. to a temperature of +25° C. and for a period of time of 1 to 18 hours.

The present invention also discloses an active catalyst system comprising the Group 4 metal single-site catalyst component of formula II and an activating agent having an alkylating/ionising action.

Suitable activating agents are well known in the art. The activating agent can be an aluminium alkyl represented by formula AlR⁺ₙX₃₋ₙ wherein R⁺ is an alkyl having from 1 to 20 carbon atoms and X is a halogen, in combination with [Ph₃C][B(C₆F₅)₄]. The preferred aluminium alkyls are triisobutyl aluminium (TIBAL) or triethyl aluminium (TEAL). Aluminium alkyls are used in combination with trityl.

Alternatively, it can be aluminoxane and comprise oligomeric linear and/or cyclic alkyl aluminoxanes represented by formula

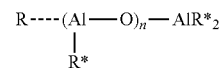

for oligomeric, linear aluminoxanes and by formula

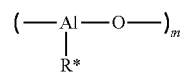

for oligomeric, cyclic aluminoxane.
wherein n is 1-40, preferably 1-20, m is 3-40, preferably 3-20 and R* is a C₁-C₈ alkyl group and preferably methyl or isobutyl.

Preferably, the activating agent is methylaluminoxane (MAO).

The amount of activating agent is selected to give an Al/M ratio of from 500 to 10000, preferably of from to 1000 to 5000. The amount of activating agent depends upon its nature.

Suitable boron-containing agents may also be used for activating Group 4 metal single-site catalyst component of formula II where R$ is an alkyl or benzyl group, These include for example a triphenylcarbenium boronate such as tetrakis-pentafluorophenyl-borato-triphenylcarbenium as described in EP-A-0427696, or those of the general formula [L'-H]+[BAr₁Ar₂X₃X₄]— as described in EP-A-0277004 (page 6, line 30 to page 7, line 7).

The amount of boron-containing activating agent is selected to give a B/M ratio of from 0.5 to 5, preferably of about 1.

In another embodiment, according to the present invention, the single-site catalyst component of formula II may be deposited on a conventional support. Preferably, the conventional support is silica impregnated with MAO. Alternatively the support may also be an activating support such as fluorinated alumina silica.

The catalyst system may comprise an optional scavenger that may be selected from triethylaluminium, triisobutylaluminum, tris-n-octylaluminium, tetraisobutyldialuminoxane or diethyl zinc.

The active Group 4 metal catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

The preferred monomer and optional comonomer can be selected from ethylene, propylene, 1-hexene or styrene. The preferred monomer is ethylene with 1-hexene as comonomer.

EXAMPLES

All experiments were performed under a purified argon atmosphere using standard Schlenk techniques, or in a glovebox. Solvents were distilled under nitrogen, from Na/benzophenone for THF and Et$_2$O, and from Na/K alloy for toluene and pentane. They were degassed thoroughly and stored under nitrogen prior to use. Deuterated solvents (benzene-d$_6$, toluene-d$_8$, THF-d$_8$; >99.5% D, Eurisotop) were vacuum-transferred from Na/K alloy into storage tubes. Tetrabenzyl M(CH$_2$Ph)$_4$ wherein M=Ti, Zr, Hf, and tetrakis(dimethylamido) Hf(NMe$_2$)$_4$ precursors, and S-Phos (dicyclohexyl(2',6'-dimethoxy-1,1'-biphenyl-2-yl)phosphine) were prepared using reported procedures. Other starting materials were purchased from Acros, Strem and Aldrich. NMR spectra of complexes were recorded on Bruker AC-200, AC-300 and AM-500 spectrometers in Teflon-valved NMR tubes at 25° C. unless otherwise indicated. $^1$H and $^{13}$C chemical shifts are reported in ppm vs. SiMe$_4$ and were determined by reference to the residual solvent peaks. Assignment of resonances for organometallic complexes was made from $^1$H-$^{13}$C HMQC and HMBC NMR experiments. Coupling constants are given in Hertz. Elemental analyses were performed by the Microanalytical Laboratory at the Institute of Chemistry of Rennes and are the average of two independent determinations.
Preparation of Ligands.
Preparation of {ONO}H$_2$ ({2-N} H$_2$).

A. Preparation of 2-(methoxymethoxy)naphthalene

To a suspension of 5.0 g of NaH (208.33 mmol) in 150 mL of DMF under argon flow were added 20.0 g of solid 2-hydroxynaphthalene (138.7 mmol) at a temperature of 0° C., by small portions. The suspension was kept under stirring for 4 h at room temperature, 17.8 g of methoxymethyl chloride (221.2 mmol) were added slowly, and the reaction mixture was stirred for 10 additional hours. The reaction was carefully diluted with 1 L of water and the organic part was extracted with 3 times 50 mL of CH$_2$Cl$_2$. The combined organic extracts were washed twice with 500 mL of water, brine and dried over MgSO$_4$. The solution was evaporated, dried in vacuum at a temperature of 80° C. to give 25.1 g of colorless oily product (133.3 mmol) that was used without further purification.

The NMR result is as follows: $^1$H NMR (200 MHz, CDCl$_3$, 25° C.): δ 7.80 (m, 3H), 7.55-7.37 (m, 3H), 7.26 (m, 1H), 5.34 (s, 2H, OCH$_2$O), 3.57 (s, 3H, OCH$_3$).
Anal. calcd. for C$_{12}$H$_{12}$O$_2$: C. 76.57; H, 6.43. Found: C, 76.59; H, 6.55.

B. Preparation of [3-(methoxymethoxy)-2-naphthyl]triphenyl)silane

A solution of 19.1 m of sec-BuLi 1.3 M in hexane/cyclohexane (24.70 mmol) was added dropwise to a stirred solution of 4.64 f of [3-(methoxymethoxy)-2-naphthyl](triphenyl)silane (24.65 mmol) in 150 mL of THF at a temperature of −78° C. over a period of time of 15 min. After stirring overnight at room temperature, to the resultant tinted solution was added a solution of 7.27 g of Ph$_3$SiCl (24.65 mmol) and 4.3 mL of HMPA (24.72 mmol) in 100 mL of THF. The reaction mixture was heated at reflux for 40 h, cooled and diluted with 1000 mL of water. The organic part was extracted with 3 times 100 mL of Et$_2$O. The combined organic extracts were dried over MgSO$_4$, and evaporated. The crude residue was recrystallised from heptane and dried under vacuum to give 8.25 g of [3-(methoxymethoxy)-2-naphthyl](triphenyl) silane (18.47 mmol) with a yield of 75%.

The NMR result is as follows: $^1$H NMR (200 MHz, CDCl$_3$, 25° C.): δ 7.83-7.75 (m, 2H), 7.72-7.58 (m, 7H), 7.55-7.25 (m, 12H), 4.96 (s, 2H, OCH$_2$O), 3.00 (s, 3H, OCH$_3$). Anal. calcd. for C$_{29}$H$_{24}$OSi: C, 83.61; H, 5.81. Found: C, 82.15; H, 5.23.

C. One Pot Synthesis of {ONO}H$_2$({2-N}H$_2$)

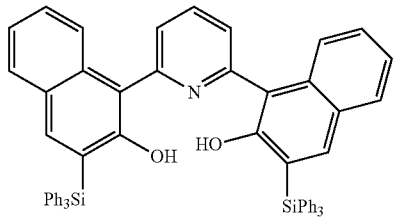

2-N

This is a one pot method comprises the following steps:
(i) To a solution of 2.3 g of [3-(methoxymethoxy)-2-naphthyl](triphenyl)silane (5.15 mmol) in 40 mL of THF were added 0.78 mL of tetramethylethylenediamine (TMEDA) (5.16 mmol) followed by addition of 4.2 mL of sec-BuLi 1.3 M in hexane/cyclohexane (5.46 mmol) at a temperature of −78° C. The reaction mixture was stirred at room temperature overnight, afterwards all the volatiles were evaporated and the residue was dried for 1 h under vacuum.
(ii) 0.70 g of anhydrous ZnCl$_2$ (5.15 mmol) were added in the glovebox, 30 mL of THF were vacuum transferred, and the resultant solution was stirred for 30 min at room temperature.
(iii) The solution was transferred to a Teflon-valved Schlenk followed by addition of 0.094 g of Pd$_2$dba$_3$ (102.6 μmol), 0.168 g of S-Phos (409.3 μmol) and 0.61 g of 2,6-dibromopyridine (2.57 mmol). The reaction mixture was stirred for 40 h at a temperature of 105° C., cooled, diluted with 200 mL of water and extracted with 3 times 20 mL of CH$_2$Cl$_2$. The combined organic extracts were dried over MgSO$_4$, and evaporated. The crude material contained about 50% of product 2,6-bis [2-(methoxymethoxy)-3-(triphenylsilyl)-1-naphthyl] pyridine as judged by $^1$H NMR spectroscopy. This material was purified by column chromatography (silica, heptane:EtOAc (15:1), R$_f$=0.12) and used without complete characterization.

(iv) The resultant solid was dissolved in a mixture of 20 mL of concentrated HCl, 30 mL of CHCl$_3$ and 40 mL of EtOH, and the solution was refluxed for 24 h. The reaction mixture was cooled to 0° C. and then carefully diluted with a concentrated solution of NaOH. Then, concentrated solution of NH$_4$Cl was added to maintain a pH value of 7-8. The product was extracted with 3 times 20 mL of CH$_2$Cl$_2$. The combined organic extracts were dried over MgSO$_4$, and evaporated to afford 1.11 g of {ONO}H$_2$ as off-white solid (1.26 mmol) with a yield of 98%.

The NMR spectra were as follows:

$^1$H NMR (500 MHz, CD$_2$Cl$_2$, 25° C.) (FIG. 5): δ 9.88 (br s, 2H, OH), 8.12 (t, J=7.9 Hz, 1H), 8.06 (m, 2H), 7.83 (m. 4H). 7.71-7.63 (m, 14H), 7.52-7.43 (m, 9H), 7.38-7.33 (m, 13H).

$^{13}$C NMR (125 MHz, CD$_2$Cl$_2$, 25° C.): δ 157.5, 155.8, 142.6, 138.3, 136.3, 134.4, 133.3, 129.5, 129.0, 128.9, 127.9, 127.8, 125.4, 124.1, 123.7, 123.4, 115.7.

Figure 4:
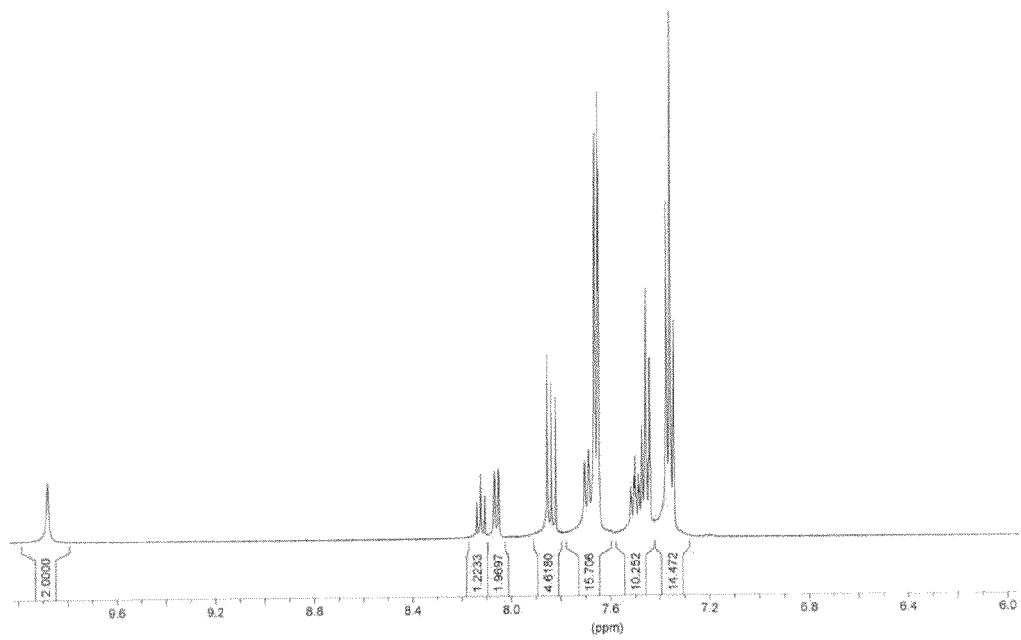
FIG. 4 represents the $^1$H NMR spectrum of {ONO}H$_2$.

The $^1$H NMR spectrum of {ONO}H$_2$ can be seen in FIG. 4.

MS-FAB (m/z): 880.3 (M$^+$).

Anal. calcd. for C$_{61}$H$_{44}$NO$_2$Si$_2$: C, 83.24; H, 5.15. Found: C, 82.76; H, 5.01.

Preparation of {OSO}H2({2-S}H2).

2-S

Using a similar synthetic approach as that described above for {ONO}H$_2$, pro-ligand {OSO}H$_2$ was prepared from 3.48 g of [3-(methoxymethoxy)-2-naphthyl](triphenyl)silane (7.79 mmol), 1.18 mL of TMEDA (7.82 mmol), 6.3 mL of sec-BuLi 1.3 M in hexane/cyclohexane (8.18 mmol), 1.06 g of ZnCl$_2$ (7.78 mmol), 0.142 g of Pd$_2$ dba$_3$ (155.0 µmol), 0.255 g of S-Phos (621.2 µmol) and 0.94 g of 2,5-dibromothiophene (3.89 mmol). The yield of (3-(methoxymethoxy)-4-{5-[2-(methoxymethoxy)-3-(triphenylsilyl)-1-naphthyl]thien-2-yl}-2-naphthyl)(triphenyl)silane after Pd-catalyzed coupling was of about 30% over 100 h. After the deprotection step and further workup, crude {OSO}H$_2$ was recovered as a deep blue powder, which was purified by passing through a short silica pad (heptane:CH$_2$Cl$_2$ (1:1)) to afford 1.01 g of colorless solid (1.14 mmol) with a yield of 98%. The NMR spectra were as follows:

$^1$H NMR (500 MHz, CDCl$_3$, 25° C.) (FIG. 6): δ 7.89 (s, 2H), 7.76 (d, J=8.6 Hz, 2H), 7.73-7.69 (m, 14H), 7.54-7.46 (m. 8H), 7.46-7.41 (m, 12H), 7.38-7.33 (m, 4H), 5.85 (s, 2H, OH).

$^{13}$C NMR (125 MHz, CDCl$_3$, 25° C.): δ 155.7, 141.9, 137.6, 136.4, 135.4, 134.3, 130.9, 129.6, 128.7, 128.6, 128.0, 127.9, 124.2, 123.6, 122.9, 112.1.

Figure 5:
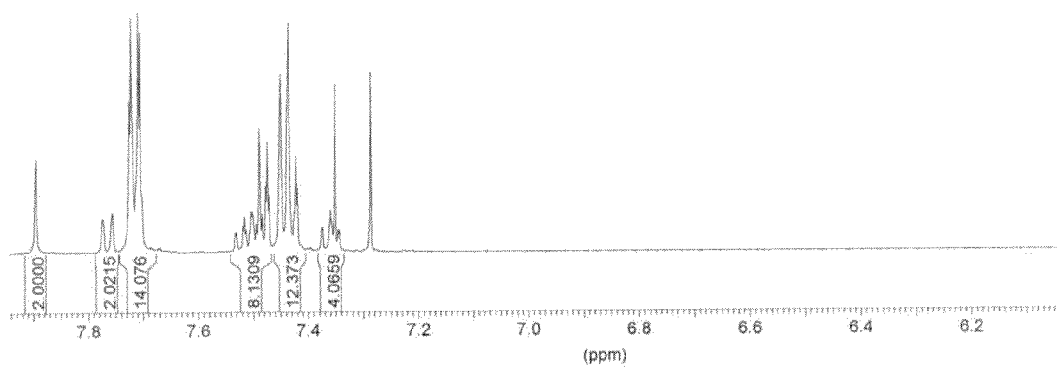
FIG. 5 represents the $^1$H NMR spectrum of {OSO}H$_2$.
Figure 6:
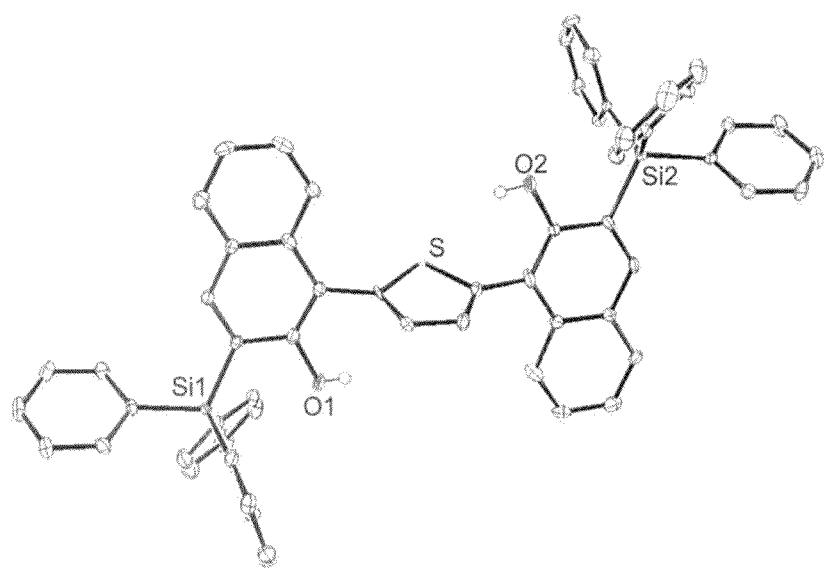
FIG. 6 represents the molecular structure of {OSO}H$_2$ pro-ligand.

The $^1$H NMR spectrum of {OSO}H$_2$ is represented in FIG. 5 and molecular structure is given in FIG. 6.

Anal. calcd. for C$_{60}$H$_{44}$O$_2$SSi$_2$: C, 81.41; H, 5.01. Found: C, 80.56; H, 4.87.

Preparation of Metallic Complexes.

Synthesis of rac-{ONO}Ti(CH$_2$Ph)$_2$.

Figure 7:
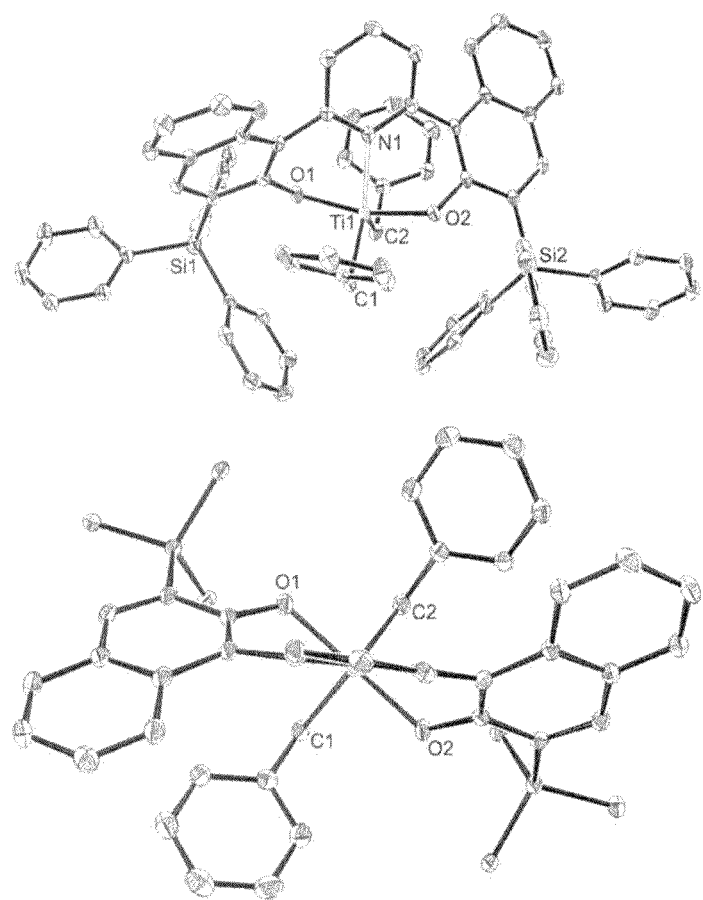
FIG. 7 represents the molecular structure of titanium metallic complex rac-{ONO}Ti(CH$_2$Ph)$_2$.

A Schlenk tube was charged with 0.20 g of {ONO}H$_2$ (0.23 mmol) and 0.094 g of Ti(CH$_2$Ph)$_4$ (0.23 mmol), and then 5 mL of toluene were vacuum transferred. The reaction mixture was stirred overnight at room temperature, filtered and evaporated and dried in vacuum to give 0.24 g of rac-{ONO}Ti(CH$_2$Ph)$_2$ as brownish-red microcrystalline material (0.22 mmol) with a yield of 95%. The molecular structure of the titanium metallic complex can be seen in FIG. 7.

The NMR spectra were as follows:

$^1$H NMR (500 MHz, toluene-d$_8$, 70° C.) (FIG. 7): δ 8.29 (s, 2H), 8.02 (m, 12H). 7.48 (d, J=8.2 Hz, 2H), 7.34 (d, J=8.2 Hz, 2H), 7.32 (d, J=8.2 Hz, 2H), 7.23 (m, 12H), 7.13 (t, J=6.8 Hz, 2H), 7.06 (m, 2H), 6.99 (m, 6H), 6.81 (t, J=8.2 Hz, 1H), 6.05 (t, J=7.5 Hz, 2H, CH$_2$Ph), 5.94 (t, J=7.5 Hz, 4H, CH$_2$Ph), 5.75 (d, J=7.5 Hz, 4H, CH$_2$Ph), 2.36 (br s, 4H, CH$_2$Ph).

$^{13}$C NMR (75 MHz, benzene-d$_6$, 25° C.): δ 161.3, 151.0, 144.1, 142.3, 137.1, 137.0, 134.6, 133.1, 129.6, 128.3, 128.1, 125.7, 125.2, 123.0, 122.9, 122.0, 121.9, 116.9 (three signals from quaternary aromatic carbons and one from CH$_2$ of the benzylic groups were not observed).

Figure 8:
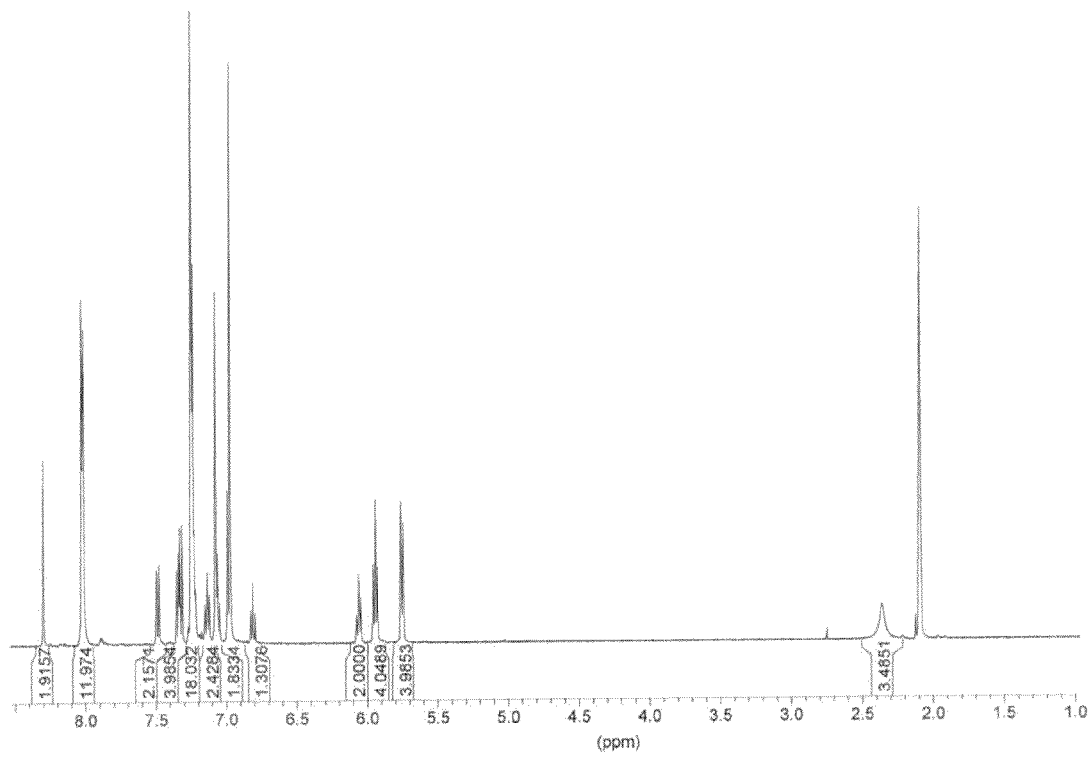
FIG. 8 represents the $^1$H NMR spectrum of titanium metallic complex rac-{ONO}Ti(CH$_2$Ph)$_2$.

The $^1$H NMR spectrum of the titanium metallic complex can be seen in FIG. 8.

Anal. calcd. for C$_{76}$H$_{57}$NO$_2$Si$_2$Ti: C, 81.28; H, 5.18. Found: C, 80.89; H, 4.97.

Synthesis of {ONO}Zr(CH$_2$Ph)$_2$

Using a procedure similar to that described hereabove 0.12 g of the zirconium complex (0.10 mmol) were obtained with a yield of 90%. It was prepared from 0.10 g of {ONO}H$_2$ (0.11 mmol) and 0.052 g of Zr(CH$_2$Ph)$_4$ (0.11 mmol).

Synthesis of meso-{ONO}Hf(NHMe$_2$)

A Schlenk tube was charged with 0.11 g of {ONO}H$_2$ (0.12 mmol) and 0.044 g of Hf(NMe$_2$)$_4$ (0.12 mmol), and 5 mL of benzene were vacuum transferred. The reaction mixture was stirred overnight at room temperature, filtered and evaporated and dried in vacuum to give 0.12 g of hafnium complex as yellow microcrystalline material (0.10 mmol) with a yield of 84%.

Figure 9:
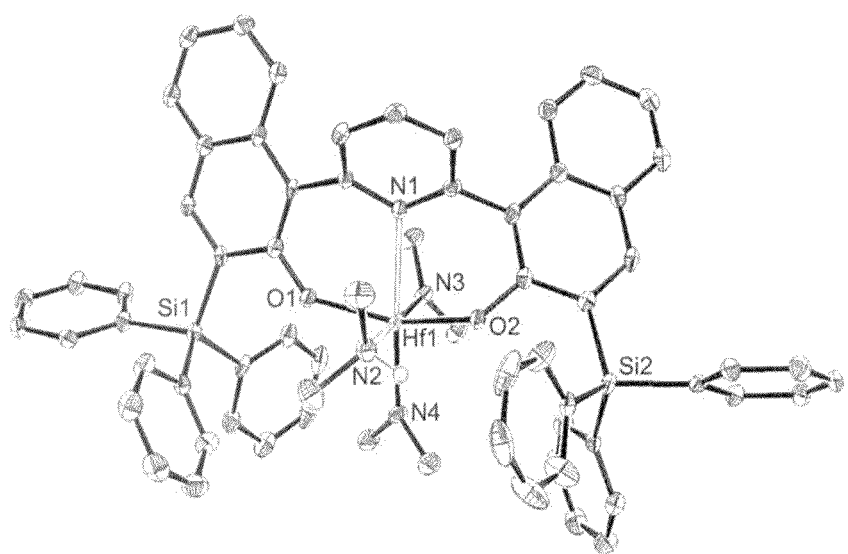
FIG. 9 represents the molecular structure of hafnium metallic complex {ONO}Hf(NMe$_2$)$_2$(NHMe$_2$).

The molecular structure of the complex can be seen in FIG. 9.

The NMR result was as follows:

$^1$H NMR (500 MHz, toluene-d$_6$, 70° C.): δ 8.40-8.20 (br m, 2H), 7.98 (br m, 9H), 7.84 (br m, 2H), 7.55-7.30 (br m, 7H), 7.28 (br m, 20H), 7.13 (br m, 3H), 3.13 (s, 12H, NMe$_2$), 2.27 (br s, 12H, NHMe$_2$) (signal from protons of NHMe$_2$ were not observed).

Anal. calcd. for C$_{67}$H$_{62}$HfN$_4$O$_2$Si$_2$: C, 67.63; H, 5.25. Found: C, 66.01; H, 4.99.

Homo or Co-Polymerisation of Ethylene.

The polymerisation was carried out as follows.

A 300 mL glass high-pressure reactor was charged with 80 mL of freshly distilled toluene and optional comonomer under argon flash. Mechanical stirring (Pelton turbine, 1000 rpm) was started, the reactor was then purged with ethylene and loaded with a solution of scavenger selected from MAO or TIBAL, at atmospheric pressure, and then kept at the desired temperature by circulating water in a double wall. A solution of trityl (if used) in 2 mL of toluene was injected in by syringe followed by injecting a solution of precatalyst in 2 mL of toluene. The gas pressure in the reactor was maintained immediately and kept constant with a back regulator throughout the experiment. The ethylene consumption was monitored via an Aalborg flowmeter. After a given time period, the reactor was depressurised and the reaction was quenched by adding about 5 mL of a 10% solution of HCl in methanol. The polymer was further precipitated by adding 500 mL of methanol, washed and dried in vacuum overnight at room temperature. The polymerisation conditions are summarised in Table I and the polymerisation results are presented in Table II.

Cat 1 is rac-{ONO}Ti(CH$_2$Ph)$_2$

Cat 2 is {ONO}Zr(CH$_2$Ph)$_2$

The monomer was ethylene.

TABLE I

| Run | Cat | Amount cat μmol | Activator | Activator/M | comonomer | T °C. | t min |
|---|---|---|---|---|---|---|---|
| 1 | cat 1 | 4.5 | MAO | 5000/1 | — | 50 | 30 |
| 2 | cat 1 | 9 | trityl/tibal | 3/200/1 | — | 50 | 10 |
| 4 | cat 2 | 9 | trityl/tibal | 3/200/1 | — | ~60 | 5 |
| 5 | cat 2 | 9 | trityl/tibal | 3/200/1 | 1-hexene | ~66 | 15 |

TABLE II

| Run | mass g | Productivity g$_{polym}$/g$_{cata}$ | Activity kg/mol/h | Mn kDa | Mw/Mn | Tm °C. |
|---|---|---|---|---|---|---|
| 1 | 0.55 | 110 | 244 | | | |
| 2 | 3.14 | 315 | 2090 | | | |
| 4 | 2.26 | 218 | 3010 | | | |
| 5 | 3.58 | 345 | 1600 | | | |

The invention claimed is:

1. A pro-ligand of general formula I:

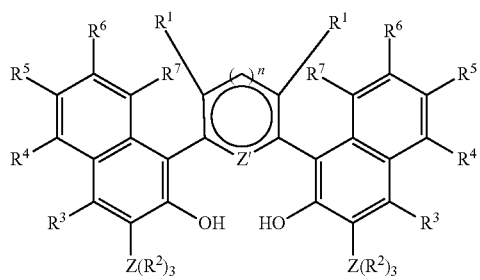

wherein R$^1$, R$^3$, R$^4$, R$^5$, R$^6$ and R$^7$ are each independently selected from hydrogen, unsubstituted or substituted hydrocarbyl, or inert functional group, wherein two or more of said groups can be linked together to form one or more rings, wherein Z' is O, S, or N=N and n is 0 or wherein n is 1 and Z' is N, Z is an atom selected from group 14 of the Periodic Table, and R$^2$ is a substituted or unsubstituted aryl group having at most 8 carbon atoms with the restriction that Z(R$^2$)$_3$ is a bulky group, at least as bulky as tertio-butyl.

2. The pro-ligand of claim 1, wherein Z is C, Si, or Ge.

3. The pro-ligand of claim 1, wherein R$^2$ is substituted or unsubstituted phenyl group.

4. The pro-ligand of claim 1, wherein R$^1$, R$^3$, R$^4$, R$^5$, R$^6$ and R$^7$ are the same and are hydrogen.

5. A method for preparing the pro-ligand of claim 1 comprising:

a) providing β-naphthol of formula

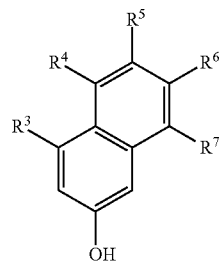

b) introducing alkoxy alkyl protecting groups by reacting with an alkoxy alkyl halide of formula XROR' wherein X is an halogen and R and R' are each independently selected from alkyl having from 1 to 6 carbon atom in the presence of dimethylformamide (DMF) and an alkali metal-alkyl or alkali metal-hydride to obtain a compound of formula:

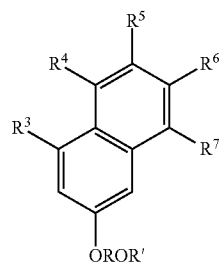

c) reacting with (R$^2$)$_3$ZX', wherein X' is an halogen, in the presence of sec-BuLi in a solvent to obtain a compound of formula:

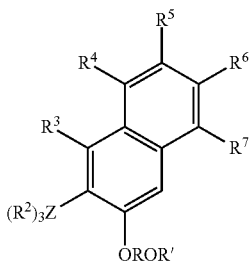

d) reacting with a dihaloheteroaryl of formula:

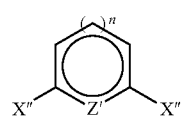

wherein Z' is O, S, or N=N and n is 0 or wherein n is 1 and Z' is N, X" is an halogen, in the presence of a palladium or nickel cross-coupling catalyst in order to obtain a compound of formula:

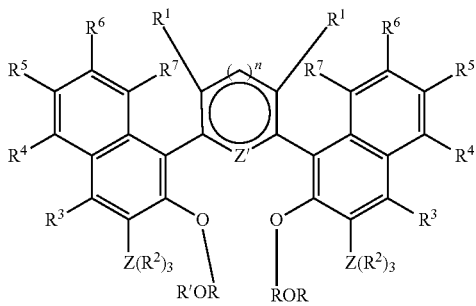

e) deprotecting the compound obtained in step d) by reaction of an acid in order to obtain a bridged pro-ligand of general formula I

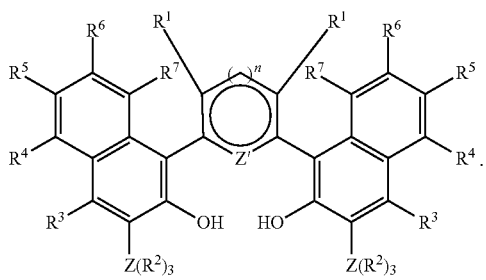

6. The method of claim 5, wherein the alkali metal-hydride comprises NaH.

7. A metallic complex of general formula

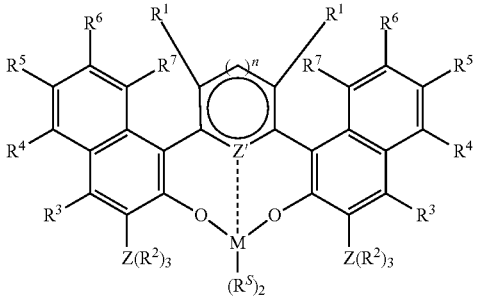

obtained by metallation reaction of the pro-ligand of claim 1 with a metallic salt of formula $MR^\$_n$ wherein M is a metal group 4 of the Periodic Table, $R^\$$ is the same or different and is an alkyl, benzyl, aryl, amido, alkoxide, halide, or combinations thereof.

8. The metallic complex of claim 7, wherein $R^\$$ is $CH_2Ph$ or $NMe_2$.

9. The metallic complex of claim 7, wherein M is Zr, Ti, or Hf.

10. An active group 4 metal catalyst system comprising the metallic complex of claim 7 and an activating agent having an ionising action.

11. A method for homo- or co-polymerising ethylene and alpha-olefins comprising:
    a) injecting the active catalyst system of claim 10 into a reactor;
    b) injecting monomer and optional comonomer into the reactor simultaneously with or after the catalyst system;
    c) maintaining the reactor under polymerising conditions; and
    d) retrieving a homo- or co-polymer of ethylene or alpha-olefin.

* * * * *